United States Patent [19]

Kamishita et al.

[11] Patent Number: 5,750,579
[45] Date of Patent: May 12, 1998

[54] QUICK-DRYING GEL-TYPE DISINFECTANT FOR HANDS AND FINGERS

[75] Inventors: Takuzo Kamishita, Takatsuki; Takashi Miyazaki, Nakaniikawa-gun, both of Japan

[73] Assignee: Toko Yakuhin Kogyo Kabushiki Kaisha, Osaka, Japan

[21] Appl. No.: 638,860

[22] Filed: Apr. 29, 1996

Related U.S. Application Data

[63] Continuation of Ser. No. 169,643, Dec. 20, 1993, abandoned.

[30] Foreign Application Priority Data

Dec. 28, 1992 [JP] Japan ................. 4-348566

[51] Int. Cl.$^6$ .............. A61K 47/32; A61K 47/36; A61L 2/18
[52] U.S. Cl. .................. 514/772.6; 514/781
[58] Field of Search ............ 424/70.122; 514/772.6, 514/781

[56] References Cited

U.S. PATENT DOCUMENTS

| | | | |
|---|---|---|---|
| 3,530,217 | 9/1970 | White et al. | 424/180 |
| 4,500,511 | 2/1985 | Kigasawa et al. | 424/78.05 |
| 4,525,348 | 6/1985 | Arizona | 424/78.05 |
| 4,540,572 | 9/1985 | Seth | 514/887 |
| 4,670,254 | 6/1987 | Kamishita et al. | 424/78.05 |
| 5,013,545 | 5/1991 | Blackman et al. | 424/445 |
| 5,098,717 | 3/1992 | Blackman | 514/648 |
| 5,158,761 | 10/1992 | Kamishita et al. | 424/464 |
| 5,158,766 | 10/1992 | Greenwald et al. | 424/78.33 |
| 5,215,739 | 6/1993 | Kamishita et al. | 424/489 |

FOREIGN PATENT DOCUMENTS

| | | |
|---|---|---|
| A-0 159 167 | 10/1985 | European Pat. Off. . |
| A-0 223 681 | 5/1987 | European Pat. Off. . |
| A-0 320 254 | 6/1989 | European Pat. Off. . |
| A-2 208 600 | 4/1989 | United Kingdom . |

OTHER PUBLICATIONS

Patent Abstract of Japan, vol. II, No. 242 (C-438) Aug. 7, 1987 & JP-A-62 051626, Mar. 6, 1987.

*Primary Examiner*—Peter F. Kulkosky
*Attorney, Agent, or Firm*—Foley & Lardner

[57] ABSTRACT

A quick-drying, gel-type disinfectant composition useful for disinfecting the hands and fingers of workers such as doctors and nurses and patients in hospitals, which can readily be used without overflowing or falling from the hands and fingers and can be well spreaded onto the hands and fingers by rubbing with neither occurrence of twisted scale-like residue nor unpleasant stickiness before or after drying, which comprises a solution of a disinfectious medicament in an alcohol and a thickening agent consisting of a combination of a carboxyvinyl polymer and a water-soluble, high molecular cellulose compound.

19 Claims, No Drawings

5,750,579

QUICK-DRYING GEL-TYPE DISINFECTANT FOR HANDS AND FINGERS

This application is a continuation of application Ser. No. 08/169,643, filed Dec. 20, 1993, now abandoned.

FIELD OF THE INVENTION

This invention relates to a quick-drying, gel-type disinfectant for the hands and fingers, more particularly to a quick-drying, gel-type disinfectant composition useful for disinfection of the hands and fingers in patients and workers in hospitals such as doctors, nurses, etc, which can easily be used and can show the desired disinfecting effects merely by applying to and rubbing into the hands and fingers, which comprises a disinfectant medicament in the form of an alcohol solution and a thickening agent consisting of a combination of a carboxyvinyl polymer and a water-soluble, high molecular cellulose compound.

PRIOR ART

Recently, it becomes a problem the subsidiary infection within a hospital, that is, workers in hospitals such as doctors and nurses or patients who enter or attend to the hospitals are sometimes suffered from various infectious diseases. Usually, pathogenic microorganisms are brought into hospitals by various routes, which causes occurrence of infections within the hospitals. It is assumed that such infections in hospitals will probably occur via the workers in hospitals, that is, the infections will be induced by cross infection with the hands and fingers of the workers in hospitals.

The infections in hospitals will be prevented in some extents by frequent washing of the hands by the workers and patients in hospitals, but it will still be difficult to completely remove the pathogenic microorganisms by washing of the hands and it will be necessary to use a disinfectant for ensuring the removal of microorganisms.

It has usually been taken to dip the hands in a basin filled with a diluted disinfectant solution in order to disinfect the hands and fingers within hospitals. However, this means of dipping hands in a basin increases rather risks of cross infection because the disinfectant solution in a basin will decrease of lose the disinfectious effect due to contamination of proteins etc. by repeatedly dipping of the hands of the users and further because the solution will be contaminated with resistant microorganisms or fallen bacteria existing in the atmosphere in hospitals.

Instead of use of the basin, recently, it has been proposed to use a compact vessel containing an alcoholic disinfectant solution which can be used personally in every time in need. This type of disinfectant for the hands and fingers, i.e. an alcoholic solution-containing vessel, has various advantages, for example, it can easily be used by merely applying to the hands and fingers a suitable amount of the disinfectant solution from the vessel when used, and it need not to wipe up with a towel etc. because the applied disinfectant solution is rupidly dried with the evaporation of the alcoholic solvent, and further, it has no risk of cross infection contrary to the means using a basin because it is not necessary to use repeatedly the same disinfectant solution.

Although this type of disinfectant with an alcoholic solution-containing vessel has recently been well used by workers such as doctors and nurses in hospitals in view of the convenient usage, it has still some defects in handling thereof due to alcoholic solution. That is, when it is used, a sufficient amount of the alcoholic solution shall be taken on the palm of the hand in oder to apply throughly to whole hands and fingers. In this case, the solution sometimes overflows the hands and falls onto the floor during taking the solution onto the palm and further during applying and rubbing the solution into the hands and fingers. Moreover, the solution overflowed or fallen may contact and denature the building interior parts or various devices in the hospitals. It should also be noted that since the solution comprises mainly a strongly flammable alcohol, such an alcoholic solution is required to be handled very carefully in view of fire prevention. Thus, although it is preferable to set in each room within the hospitals so as to provide free and ready use by any person, it will be not preferable to do so from the viewpoint of fire prevention.

BRIEF DESCRIPTION OF THE INVENTION

In view of the defects of the disinfectant of an alcoholic solution-containing vessel as mentioned above, the present inventors have intensively studied to find any other type of disinfectant suitable for disinfecting the hands and fingers and had an idea to increase the viscosity of the alcoholic solution by gelling thereof for the purpose of eliminating the defects of overflowing or falling of the solution. Thus, the inventors have tried to increase the viscosity of the alcoholic solution with a carboxyvinyl polymer which has widely been used as a thickening agent in various fields of technique and have found that it can give a certain gel-type disinfectant composition which can be used without defects such as overflowing or falling. However, this gel-type disinfectant has still a problem that it remains a twisted scale-like residue on the hands and fingers due to precipitation (resin-formation) of the polymer component when rubbed into the hands and fingers. As a result of further intensive studies by the present inventors for the purpose of obtaining the desired disinfectant which can be well spreaded onto the hands and fingers by rubbing with neither occurrence of undesirable twisted scale-like residue nor unpleasant stickiness before or after drying (and hence no need of washing or wiping up with towel), it has been found that the desired gel-type disinfectant composition having excellent physical properties and effects can be prepared by incorporating a thickening agent consisting of a combination of a carboxyvinyl polymer and a water-soluble, high molecular cellulose compound to an alcoholic solution containing an active disinfectious medicament (antimicrobials), and thereby, the present invention has been accomplished.

Thus, an object of the invention is to provide a quick-drying, gel-type disinfectant for the hands and fingers which comprises an alcoholic solution containing an active disinfectious medicament and a thickening agent consisting of a combination of a carboxyvinyl polymer and a water-soluble, high molecular cellulose compound. One of the two components of the thickening agent, the carboxyvinyl polymer is effective for gelling the alcoholic solution and for modifying the solution so that it can be well spreaded onto whole the hands and fingers without unpleasant stickiness before or after drying, and another of the two components, the water-soluble, high molecular cellulose compound is effective for eliminating the defect of occurrence of undesirable twisted scale-like residue when rubbed the composition into the hands and fingers. The desired composition having excellent properties and effects can be obtained by using this specific combination of the two components as a thickening agent.

DETAILED DESCRIPTION OF THE INVENTION

The quick-drying, gel-type disinfectant composition for the hands and fingers of the present invention comprises 0.01 to 5.0% by weight of the active disinfectious medicament (antimicrobials), 40 to 90% by weight of an alcohol, and 0.05 to 2.0% by weight of a carboxyvinyl polymer and 0.1 to 2.5% by weight of a water-soluble, high molecular cellulose compound as the thickening agent, wherein the total amount of the carboxyvinyl polymer and the water-soluble, high molecular cellulose compound is not more than 3.0% by weight, these weight percentages of the components being based on the whole weight of the composition. When the carboxyvinyl polymer is incorporated in an amount of less than 0.05% by weight, the prepared disinfectant composition does not have sufficient viscosity suitable for use, but on the other hand, when the amount is over 2.0% by weight, the composition has too high viscosity and hence is hardly handled. Likewise, when the water-soluble, high molecular cellulose compound is incorporated in an amount of less than 0.1% by weight, the prepared disinfectant composition does not have sufficient viscosity suitable for use, but on the other hand, when the amount is over 2.5% by weight, the composition has too high viscosity and hence is hardly handled. These components of thickening agent are incorporated in such an amount that the disinfectant composition can show a viscosity suitable for spreading onto the hands and fingers without falling from the hands and fingers when applied, and for such a purpose, both components are used in an amount of not more than 3.0% by weight in total within the above ranges of amount of each component.

Thus, the quick-drying, gel-type disinfectant composition for the hands and fingers of the present invention has a viscosity in such a range that the composition is not fallen from the hands and fingers when applied, that is, in the range of about 500 to 50,000 centipoises at 20° C.

The disinfectant composition of the present invention may further be incorporated with a water-soluble basic compound such as organic amines (e.g. triethanolamine, diisopropanolamine, etc.) or inorganic basic compounds (e.g. sodium hydroxide, potassium hydroxide, etc.) in order to regulate the pH 4 to 8 and also to gelate the composition. The composition may further optionally be incorporated with other additives used for conventional agents for dermatologic use such as wetting agents, antioxidants, perservatives, etc. Particularly, it is preferable to incorporate a wetting agent into the disinfectant composition in order to prevent any possible chapping of skin due to defatting by the alcoholic gel. Suitable examples of the wetting agent are glycerin, propylene glycol, sorbitol, 1,3-butylene glycol, polyethylene glycol, hyaluronic acid, urea, sodium pyrrolidonecarboxylate, and the like, which are used alone or in combination of two or more thereof in an amount of 0.1 to 5.0% by weight based on the whole weight of the composition.

The active antimicrobials to be contained as an active disinfectious medicament in the composition are, for example, invert soaps such as benzalkonium chloride or benzethonium chloride; biguanide compounds such as chlorhexidine salts; phenol compounds such as cresol; iodine compounds such as povidone-iodine; and pigment compounds such as acrinol, which may be used alone or in combination of two or more thereof. These disinfectious medicaments are contained in the form of an alcohol solution. The alcohol includes methanol, ethanol, isopropanol, and the like, preferably ethanol or isopropanol, or a mixture thereof.

The carboxyvinyl polymer used as one of the thickening agent includes any commertially available compounds, such as Carbopol 941, Carbopol 934, Carbopol 934P, Carbopol 940, Carbopol 1342, Carbopol 981, Carbopol 974, Carbopol 2984, Carbopol 5984, Carbopol 980, Carbopol 1382, which are all manufactured and sold by B. F. Goodrich.

The water-soluble, high molecular cellulose compound used as another one of the thickening agent includes, for example, methyl cellulose, ethyl cellulose, hydroxyethyl cellulose, hydroxypropyl cellulose, carboxymethyl cellulose, hydroxypropylmethyl cellulose, and the like.

The thickening agent used for the disinfectant composition of the present invention consists essentially of a combination of one or more of the water-soluble, high molecular cellulose compound and the carboxyvinyl polymer, and when any one of these components is used alone, the desired composition can not be obtained. That is, when the carboxyvinyl polymer is used alone, the composition has a sufficiently decreased viscosity and can well be spreaded onto the hands and fingers, but when applied to, the polymer component precipitates (forms resin) by the action of the salts (e.g. sodium chloride) on the hands and fingers to give twisted scale-like residue. On the other hand, when the water-soluble, high molecular cellulose compound is used alone, the composition shows inferior spreading property and hence can hardly be spreaded onto the hands and fingers and further shows disadvantageously high stickiness before and after drying.

EXAMPLES

The present invention is illustrated by the following Examples but should not be construed to be limited thereto. In Examples, the viscosity is measured with type C viscometer (manufactured by Tokyo Keiki Kabushiki Kaisha) at 20° C.

Example 1

A quick-drying, gel-type disinfectant composition for the hands and fingers is prepared in the following formulation.

| | |
|---|---|
| Benzalkonium chloride | 0.22 g |
| Ethanol defined in Japan Pharmacopeia | 78.5 g |
| Glycerin | 0.2 g |
| Carboxyvinyl polymer (Carbopol 940) | 0.8 g |
| Hydroxypropylmethyl cellulose | 0.5 g |
| Diisopropanolamine | 0.38 g |
| Purified water | 19.40 g |

Benzalkonium chloride (0.22 g) is dissolved in ethanol (Japan Pharmacopeia) (78.5 g) and thereto is added glycerin (0.2 g). The mixture is stirred and thereto is homogeneously dispersed hydroxypropylmethyl cellulose (0.5 g).

Separately, the carboxyvinyl polymer (0.8 g) is added to purified water (19.40 g) and the mixture is stirred to give a homogeneous solution. The solution is gelled by adding thereto diisopropanolamine (0.38 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 20,000 centipoises and pH 6.0.

Example 2

A quick-drying, gel-type disinfectant composition for the hands and fingers is prepared in the following formulation.

| | |
|---|---|
| Benzalkonium chloride | 0.22 g |
| Ethanol defined in Japan Pharmacopeia | 58.5 g |
| Isopropanol | 20.0 g |
| Glycerin | 0.2 g |
| Carboxyvinyl polymer (Carbopol 940) | 0.5 g |
| Ethyl cellulose | 1.0 g |
| Diisopropanolamine | 0.25 g |
| Purified water | 19.33 g |

Benzalkonium chloride (0.22 g) is dissolved in ethanol (Japan Pharmacopeia) (58.5 g) and isopropanol (20.0 g), and thereto is added glycerin (0.2 g). The mixture is stirred and thereto is homogeneously dispersed ethyl cellulose (1.0 g).

Separately, the carboxyvinyl polymer (0.5 g) is added to purified water (19.33 g) and the mixture is stirred to give a homogeneous solution. The solution is gelled by adding thereto diisopropanolamine (0.25 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 7,400 centipoises and pH 7.10.

Example 3

A quick-drying, gel-type disinfectant composition for the hands and fingers is prepared in the following formulation.

| | |
|---|---|
| Conc. benzalkonium chloride solution 50 (50% aqueous benzalkonium chloride solution) | 0.6 g |
| Ethanol defined in Japan Pharmacopeia | 80.0 g |
| 1,3-Butylene glycol | 0.5 g |
| Carboxyvinyl polymer (Carbopol 940) | 0.4 g |
| Hydroxypropylmethyl cellulose | 0.5 g |
| Diisopropanolamine | 0.3 g |
| Purified water | 17.7 g |

Conc. benzalkonium chloride solution 50 (0.6 g) is dissolved in ethanol (Japan Pharmacopeia) (80.0 g) and thereto is added 1,3-butylene glycol (0.5 g). The mixture is stirred and thereto is homogeneously dispersed hydroxypropylmethyl cellulose (0.5 g).

Separately, the carboxyvinyl polymer (0.4 g) is added to purified water (17.7 g) and the mixture is stirred to give a homogeneous solution. The solution is gelled by adding thereto diisopropanolamine (0.3 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 5,000 centipoises and pH 7.50.

Example 4

A quick-drying, gel-type disinfectant composition for the hands and fingers is prepared in the following formulation.

| | |
|---|---|
| Conc. benzalkonium chloride solution 50 (50% aqueous benzalkonium chloride solution) | 0.6 g |
| Isopropanol | 50.0 g |
| 1,3-Butylene glycol | 0.5 g |
| Carboxyvinyl polymer (Carbopol 940) | 1.0 g |
| Hydroxypropylmethyl cellulose | 1.5 g |
| Triethanolamine | 1.4 g |
| Purified water | 45.0 g |

Conc. benzalkonium chloride solution 50 (0.6 g) is dissolved in isopropanol (50.0 g) and thereto is added 1,3-butylene glycol (0.5 g). The mixture is stirred and thereto is homogeneously dispersed hydroxypropylmethyl cellulose (1.5 g).

Separately, the carboxyvinyl polymer (1.0 g) is added to purified water (45.0 g) and the mixture is stirred to give a homogeneous solution. The solution is gelled by adding thereto triethanolamine (1.4 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 30,000 centipoises and pH 7.20.

Example 5

A quick-drying, gel-type disinfectant composition for the hands and fingers is prepared in the following formulation.

| | |
|---|---|
| Benzethonium chloride | 0.2 g |
| Ethanol defined in Japan Pharmacopeia | 78.5 g |
| Propylene glycol | 0.2 g |
| Carboxyvinyl polymer (Carbopol 940) | 0.75 g |
| Hydroxypropyl cellulose | 1.5 g |
| Diisopropanolamine | 0.38 g |
| Purified water | 18.47 g |

Benzethonium chloride (0.2 g) is dissolved in ethanol (Japan Pharmacopeia) (78.5 g) and thereto is added propylene glycol (0.2 g). The mixture is stirred and thereto is homogeneously dispersed hydroxypropyl cellulose (1.5 g).

Separately, the carboxyvinyl polymer (0.75 g) is added to purified water (18.47 g) and the mixture is stirred to give a homogeneous solution. The solution is gelled by adding thereto diisopropanolamine (0.38 g) and the mixture is well stirred until it becomes homogeneous. To the resulting gel is added the above-obtained solution of benzethonium chloride, and the mixture is stirred until it becomes homogeneous, by which there is prepared a colorless and clear quick-drying, gel-type disinfectant composition for the hands and fingers.

The composition thus obtained has a viscosity of 35,000 centipoises and pH 6.95.

Example 6

A quick-drying, gel-type disinfectant composition for the hands and fingers is prepared in the following formulation.

| | |
|---|---|
| Benzethonium chloride | 0.2 g |
| Isopropanol | 50.0 g |
| Polyethylene glycol 400 | 0.2 g |
| Carboxyvinyl polymer (Carbopol 940) | 0.75 g |

| | |
|---|---|
| Methyl cellulose | 0.5 g |
| Diisopropanolamine | 0.38 g |
| Purified water | 47.97 g |

Benzethonium chloride (0.2 g) is dissolved in isopropanol (50.0 g), and thereto is added polyethylene glycol 400 (0.2 g). The mixture is stirred and thereto is homogeneously dispersed methyl cellulose (0.5 g).

Separately, the carboxyvinyl polymer (0.75 g) is added to purified water (47.97 g) and the mixture is stirred to give a homogeneous solution. The solution is gelled by adding thereto diisopropanolamine (0.38 g) and the mixture is well stirred until it becomes homogeneous. To the resulting gel is added the above-obtained solution of benzethonium chloride, and the mixture is stirred until it becomes homogeneous, by which there is prepared a colorless and clear quick-drying, gel-type disinfectant composition for the hands and fingers.

The composition thus obtained has a viscosity of 9,000 centipoises and pH 6.90.

Example 7

A quick-drying, gel-type disinfectant composition for the hands and fingers is prepared in the following formulation.

| | |
|---|---|
| Conc. benzalkonium chloride solution 50 | 0.4 g |
| (50% aqueous benzalkonium chloride solution) | |
| Ethanol defined in Japan Pharmacopeia | 75.0 g |
| 1,3-Butylene glycol | 0.2 g |
| Carboxyvinyl polymer (Carbopol 940) | 0.1 g |
| Hydroxypropylmethyl cellulose | 0.2 g |
| Diisopropanolamine | 0.048 g |
| Purified water | 24.052 g |

Conc. benzalkonium chloride solution 50 (0.4 g) is dissolved in ethanol (Japan Pharmacopeia) (75.0 g) and thereto is added 1,3-butylene glycol (0.2 g). The mixture is stirred and thereto is homogeneously dispersed hydroxypropylmethyl cellulose (0.2 g).

Separately, the carboxyvinyl polymer (0.1 g) is added to purified water (24.052 g) and the mixture is stirred to give a homogeneous solution. The solution is gelled by adding thereto diisopropanolamine (0.048 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 750 centipoises and pH 6.95.

Example 8

A quick-drying, gel-type disinfectant composition for the hands and fingers is prepared in the following formulation.

| | |
|---|---|
| Conc. benzalkonium chloride solution 50 | 0.4 g |
| (50% aqueous benzalkonium chloride solution) | |
| Ethanol defined in Japan Pharmacopeia | 75.0 g |
| 1,3-Butylene glycol | 0.2 g |
| Carboxyvinyl polymer (Carbopol 940) | 0.65 g |
| Hydroxypropylmethyl cellulose | 0.5 g |
| Diisopropanolamine | 0.4 g |
| Purified water | 22.85 g |

Conc. benzalkonium chloride solution 50 (0.4 g) is dissolved in ethanol (Japan Pharmacopeia) (75.0 g) and thereto is added 1,3-butylene glycol (0.2 g). The mixture is stirred and thereto is homogeneously dispersed hydroxypropylmethyl cellulose (0.5 g).

Separately, the carboxyvinyl polymer (0.65 g) is added to purified water (22.85 g) and the mixture is stirred to give a homogeneous solution. The solution is gelled by adding thereto diisopropanolamine (0.4 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 7,800 centipoises and pH 7.50.

Example 9

A quick-drying, gel-type disinfectant composition for the hands and fingers is prepared in the following formulation.

| | |
|---|---|
| Conc. benzalkonium chloride solution 50 | 0.4 g |
| (50% aqueous benzalkonium chloride solution) | |
| Ethanol defined in Japan Pharmacopeia | 75.0 g |
| 1,3-Butylene glycol | 0.2 g |
| Carboxyvinyl polymer (Carbopol 940) | 1.0 g |
| Hydroxypropylmethyl cellulose | 1.5 g |
| Diisopropanolamine | 0.48 g |
| Purified water | 21.42 g |

Conc. benzalkonium chloride solution 50 (0.4 g) is dissolved in ethanol (Japan Pharmacopeia) (75.0 g) and thereto is added 1,3-butylene glycol (0.2 g). The mixture is stirred and thereto is homogeneously dispersed hydroxypropylmethyl cellulose (1.5 g).

Separately, the carboxyvinyl polymer (1.0 g) is added to purified water (21.42 g) and the mixture is stirred to give a homogeneous solution. The solution is gelled by adding thereto diisopropanolamine (0.48 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 45,000 centipoises and pH 7.05.

Example 10

A quick-drying, gel-type disinfectant composition for the hands and fingers is prepared in the following formulation.

| | |
|---|---|
| Conc. benzalkonium chloride solution 50 | 0.6 g |
| (50% aqueous benzalkonium chloride solution) | |
| Ethanol defined in Japan Pharmacopeia | 75.0 g |
| 1,3-Butylene glycol | 0.2 g |
| Carboxyvinyl polymer (Carbopol 940) | 0.78 g |
| Hydroxypropylmethyl cellulose | 0.5 g |

| | |
|---|---|
| Diisopropanolamine | 0.38 g |
| Purified water | 22.54 g |

Conc. benzalkonium chloride solution 50 (0.6 g) is dissolved in ethanol (Japan Pharmacopeia) (75.0 g) and thereto is added 1,3-butylene glycol (0.2 g). The mixture is stirred and thereto is homogeneously dispersed hydroxypropylmethyl cellulose (0.5 g).

Separately, the carboxyvinyl polymer (0.78 g) is added to purified water (22.54 g) and the mixture is stirred to give a homogeneous solution. The solution is gelled by adding thereto diisopropanolamine (0.38 g) and the mixture is well stirred until it becomes homogeneous. To the resulting gel is added the above-obtained solution of benzalkonium chloride, and the mixture is stirred until it becomes homogeneous, by which there is prepared a colorless and clear quick-drying, gel-type disinfectant composition for the hands and fingers.

The composition thus obtained has a viscosity of 7,000 centipoises and pH 6.95.

Example 11

By using the same components as used in Example 10 except that hydroxypropylmethyl cellulose (1.0 g) and purified water (22.04 g) are used, there is prepared a quick-drying, gel-type disinfectant composition for the hands and fingers. The composition thus obtained has a viscosity of 15,000 centipoises and pH 6.95.

Example 12

By using the same components as used in Example 10 except that hydroxypropylmethyl cellulose (1.5 g) and purified water (21.54 g) are used, there is prepared a quick-drying, gel-type disinfectant composition for the hands and fingers. The composition thus obtained has a viscosity of 28,000 centipoises and pH 6.95.

Example 13

A quick-drying, gel-type disinfectant composition for the hands and fingers is prepared in the following formulation.

| | |
|---|---|
| Chlorhexidine gluconate solution | 0.5 ml |
| (20 w/v % aqueous chlorhexidine gluconate solution) | (0.53 g) |
| Ethanol defined in Japan Pharmacopeia | 78.5 g |
| Glycerin | 0.2 g |
| Carboxyvinyl polymer (Carbopol 940) | 0.75 g |
| Hydroxypropylmethyl cellulose | 1.0 g |
| Diisopropanolamine | 0.38 g |
| Purified water | 18.64 g |

Glycerin (0.2 g) is added to ethanol (Japan Pharmacopeia) (78.5 g). After stirring the mixture, hydroxy-propylmethyl cellulose (1.0 g) is homogeneously dispersed thereto.

Separately, the carboxyvinyl polymer (0.75 g) is added to purified water (18.64 g) and the mixture is stirred to give a homogeneous solution. The solution is gelled by adding thereto diisopropanolamine (0.38 g) and the mixture is well stirred until it becomes homogeneous. To the resulting gel is added the above-obtained chlorhexidine gluconate solution (0.5 ml), and the mixture is stirred until it becomes homogeneous, by which there is prepared a colorless and clear quick-drying, gel-type disinfectant composition for the hands and fingers.

The composition thus obtained has a viscosity of 15,000 centipoises and pH 6.85.

Example 14

A quick-drying, gel-type disinfectant composition for the hands and fingers is prepared in the following formulation.

| | |
|---|---|
| Chlorhexidine gluconate solution | 2.5 ml |
| (20 w/v % aqueous chlorhexidine gluconate solution) | (2.65 g) |
| Ethanol defined in Japan Pharmacopeia | 75.0 g |
| Propylene glycol | 0.8 g |
| Carboxyvinyl polymer (Carbopol 940) | 0.5 g |
| Hydroxypropylmethyl cellulose | 1.0 g |
| Diisopropanolamine | 0.24 g |
| Purified water | 19.81 g |

Propylene glycol (0.8 g) is added to ethanol (Japan Pharmacopeia) (75.0 g). After stirring the mixture, hydroxypropylmethyl cellulose (1.0 g) is homogeneously dispersed thereto.

Separately, the carboxyvinyl polymer (0.5 g) is added to purified water (19.81 g) and the mixture is stirred to give a homogeneous solution. The solution is gelled by adding thereto diisopropanolamine (0.24 g) and the mixture is well stirred until it becomes homogeneous. To the resulting gel is added the above-obtained chlorhexidine gluconate solution (2.5 ml), and the mixture is stirred until it becomes homogeneous, by which there is prepared a colorless and clear quick-drying, gel-type disinfectant composition for the hands and fingers.

The composition thus obtained has a viscosity of 6,500 centipoises and pH 6.90.

Example 15

A quick-drying, gel-type disinfectant composition for the hands and fingers is prepared in the following formulation.

| | |
|---|---|
| Cresol | 0.5 g |
| Ethanol defined in Japan Pharmacopeia | 80.0 g |
| Glycerin | 0.1 g |
| Carboxyvinyl polymer (Carbopol 940) | 0.2 g |
| Hydroxypropylmethyl cellulose | 0.8 g |
| Diisopropanolamine | 0.1 g |
| Purified water | 18.3 g |

Cresol (0.5 g) is mixed with ethanol (Japan Pharmacopeia) (80.0 g) and thereto is added glycerin (0.1 g). The mixture is stirred and thereto is homogeneously dispersed hydroxypropylmethyl cellulose (0.8 g).

Separately, the carboxyvinyl polymer (1.0 g) is added to purified water (18.3 g) and the mixture is stirred to give a homogeneous solution. The solution is gelled by adding thereto diisopropanolamine (0.5 g) and the mixture is well stirred until it becomes homogeneous. To the resulting gel is added the above-obtained cresol solution, and the mixture is stirred until it becomes homogeneous, by which there is prepared a colorless and clear quick-drying, gel-type disinfectant composition for the hands and fingers.

The composition thus obtained has a viscosity of 13,000 centipoises and pH 7.35.

The gel-type disinfectant composition of the present invention can be used for disinfecting the hands and fingers without defects such as overflowing or falling and can be well spreaded onto the hands and fingers when rubbed with neither occurrence of twisted scale-like residue on the hands and fingers nor unpleasant stickiness before or after drying and hence is readily useful for disinfecting the hands and fingers of doctors, nurses and patients in hospitals without necessity of washing or wiping up with towel.

What is claimed is:

1. In a method for controlling the viscosity of a composition comprising a solution of a disinfectious medicament selected from the group consisting of invert soaps, biguanide compounds, phenol compounds, iodine compounds, pigment compounds, and a mixture of two or more thereof in an alcohol, by a thickening agent, which comprises using as the only thickening agent a thickening agent consisting of a combination of a carboxyvinyl polymer and hydroxypropylmethyl cellulose.

2. The method as claimed in claim 1, wherein the carboxyvinyl polymer is used in an amount of 0.05 to 2.0% by weight, and the hydroxypropylmethyl cellulose is used in an amount of 0.1 to 2.5% by weight, provided that the total weight of both components is not larger than 3.0% by weight.

3. A quick-drying gel-type disinfectant composition which comprises a solution of a disinfectious medicament selected from the group consisting of invert soaps, biguanide compounds, phenol compounds, iodine compounds, pigment compounds, and a mixture of two or more thereof in an alcohol;

and as the only thickening agent a thickening agent consisting of a combination of a carboxyvinyl polymer and hydroxypropylmethyl cellulose, wherein the carboxyvinyl polymer is contained in an amount of 0.05 to 2.0% by weight of the composition, and the hydroxypropylmethyl cellulose is contained in an amount of 0.1 to 2.5% by weight of the composition, provided that the total weight of both components is not larger than 3.0% by weight, and wherein the composition has a pH value in the range of 4 to 8 and a viscosity of about 500 to 50,000 centipoise at 20° C.

4. A method for disinfection of hands and fingers of patients and workers in hospitals, which comprises applying a composition comprising a solution of a disinfectious medicament in an alcohol and as the only thickening agent a thickening agent consisting of a combination of a carboxyvinyl polymer and hydroxypropyl methyl cellulose, wherein the carboxyvinyl polymer is contained in an amount of 0.05 to 2.0% by weight, and the hydroxypropyl methyl cellulose is contained in an amount of 0.1 to 2.5% by weight, provided that the total weight of both components is not larger than 3.0% by weight, and wherein the composition has a pH value in the range of 4 to 8 and a viscosity of about 500 to 50,000 centipoise at 20° C.

to the entire hands and fingers of patients and workers in hospitals, whereby the applied composition dries rapidly without falling off the hands or fingers, and without the necessity for washing or wiping with a towel, and wherein after application the treated hands and fingers do not have unpleasant stickiness or contain scale-like residue.

5. The disinfectant composition as claimed in claim 3, which further comprises a wetting agent selected from the group consisting of glycerin, propylene glycol, sorbitol, 1,3-butylene glycol, polyethylene glycol, hyaluronic acid, urea, and sodium pyrrolidonecarboxylate, and a mixture of two or more thereof.

6. The disinfectant composition as claimed in claim 3, wherein the alcohol is a member selected from the group consisting of methanol, ethanol, and isopropanol, and a mixture of two or more thereof.

7. The method as claimed in claim 4, wherein the disinfectious medicament is a member selected from the group consisting of invert soaps, biguanide compounds, phenol compounds, iodine compounds, pigment compounds, and a mixture of two or more thereof.

8. The disinfectant composition as claimed in claim 3, which comprises 0.01 to 5.0% by weight of the disinfectious medicament and 40 to 90% by weight of alcohol.

9. The disinfectant composition as claimed in claim 3, which comprises a water-soluble basic compound in order to maintain the pH in the range of 4 to 8 and to gelate the composition.

10. The disinfectant composition as claimed in claim 3, wherein the disinfectious medicament comprises benzalkonium chloride.

11. The disinfectant composition as claimed in claim 3, wherein the disinfectious medicament comprises benzalkonium chloride or benzethonium chloride.

12. The disinfectant composition as claimed in claim 3, wherein the disinfectious medicament comprises a chlorhexidine salt.

13. The disinfectant composition as claimed in claim 3, wherein the disinfectious medicament comprises cresol.

14. The disinfectant composition as claimed in claim 3, wherein the disinfectious medicament comprises povidone-iodine.

15. The disinfectant composition as claimed in claim 3, wherein the disinfectious medicament comprises acrinol.

16. A method as claimed in claim 4, wherein the composition further comprises a wetting agent and a water-soluble basic compound.

17. A composition as claimed in claim 3, wherein the composition further comprises a wetting agent and a water-soluble basic compound.

18. A method as claimed in claim 16, wherein the wetting agent comprises glycerin and the water-soluble basic compound comprises diisopropanol amine.

19. A composition as claimed in claim 17, wherein the wetting agent comprises glycerin and the water-soluble basic compound comprises diisopropanol amine.

* * * * *